(12) United States Patent
Bertin et al.

(10) Patent No.: US 9,850,444 B2
(45) Date of Patent: Dec. 26, 2017

(54) UNSATURATED POLYOL ESTERS USED IN HYDRAULIC FLUID APPLICATIONS

(71) Applicant: Elevance Renewable Sciences, Inc., Woodridge, IL (US)

(72) Inventors: Paul A. Bertin, Western Springs, IL (US); Courtnay Shaner, Woodridge, IL (US); Na Liu, Aurora, IL (US); Monika Mujkic, Central, SC (US); Kristine Counter, Elgin, IL (US); Jonathan Brekan, La Grange, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/803,780

(22) Filed: Jul. 20, 2015

(65) Prior Publication Data

US 2016/0016879 A1 Jan. 21, 2016

Related U.S. Application Data

(60) Provisional application No. 62/105,856, filed on Jan. 21, 2015, provisional application No. 62/026,995, filed on Jul. 21, 2014.

(51) Int. Cl.
*C10M 105/38* (2006.01)
*C07C 69/533* (2006.01)

(52) U.S. Cl.
CPC ......... *C10M 105/38* (2013.01); *C07C 69/533* (2013.01); *C10M 2207/2835* (2013.01)

(58) Field of Classification Search
CPC ............... C07C 69/533; C10M 105/38; C10M 2207/2835
See application file for complete search history.

(56) References Cited

U.S. PATENT DOCUMENTS

| 4,545,941 A | 10/1985 | Rosenburg |
| 6,943,262 B2 | 9/2005 | Kodali et al. |

FOREIGN PATENT DOCUMENTS

WO WO2012129477 * 9/2012

OTHER PUBLICATIONS

Fandino et al., Green Chem, vol. 7, pp. 775-783 (2005).
Kaushik et al., Int'l J. Polymer Anal. Charact., vol. 10, pp. 373-386 (2005).
Gunam Resul et al, "Synthesis of Biodegradable Lubricant from Jatropha Oil with High Content of Free Fatty Acids," Am. Inst. Chem. Eng., 2008 Annual Meeting (2008).
Int'l Search Report & Written Opinion of Int'l Searching Authority, PCT App. No. PCT/US2015/041154, dated Sep. 25, 2015.

* cited by examiner

*Primary Examiner* — Pancham Bakshi
*Assistant Examiner* — Mark Luderer
(74) *Attorney, Agent, or Firm* — Kilpatrick Townsend & Stockton LLP

(57) ABSTRACT

This invention relates to unsaturated polyol esters that can be used in hydraulic fluid applications, including fire-resistant hydraulic fluid applications, marine hydraulic fluid applications, metalworking fluid applications, food grade fluid applications, and transformer fluid applications, and methods for making the same.

6 Claims, No Drawings

UNSATURATED POLYOL ESTERS USED IN HYDRAULIC FLUID APPLICATIONS

CROSS REFERENCE TO RELATED APPLICATIONS

A claim of priority for this application under 35 U.S.C. §119(e) is hereby made to U.S. Provisional Patent Application No. 62/105,856, filed Jan. 21, 2015, and U.S. Provisional Patent Application No. 62/026,995, filed Jul. 21, 2014, which are hereby incorporated by reference in their entireties.

FIELD OF THE INVENTION

This patent application relates to unsaturated polyol esters that can be used in hydraulic fluid applications, including fire-resistant hydraulic fluid applications, marine hydraulic fluid applications, metalworking fluid applications, food grade fluid applications, and transformer fluid applications, and methods of making the same.

BACKGROUND OF THE INVENTION

Hydraulic fluids are used in industrial machinery that perform work through the transfer of power from one location to another. Current hydraulic systems are often complicated, and involve motors, actuators, gear, vane, and piston pumps to convert hydraulic power into useful work. In addition to transferring power, hydraulic fluids must lubricate, transfer heat, and be compatible with other materials such as gaskets, seals, and metal components in the system.

While most commercially available hydraulic fluids are petroleum based, the increasingly important issues of environmental acceptance and biodegradability are drivers behind the desire for alternatives to petroleum based hydraulic fluids. It has been reported that over 60% of all lubricants end up in our soil and water, and such releases can cause contamination of the soil, ground, and surface water. A biodegradable option in hydraulic fluids are natural oil based polyol esters. Polyol esters are products of the transesterification of one or more fatty acids or fatty acid esters with one or more polyhydric alcohols. Such polyol esters are also lighter than water and not miscible with water, so they can be removed from wastewater streams via skimming.

One category of hydraulic fluids are fire-resistant hydraulic fluids. Fire-resistant hydraulic fluids must meet at least the following three fundamental requisites: (i) a high degree of flame propagation resistance; (ii) a lubricity adequate to the operating conditions existing in the hydraulic system; (iii) a high operational stability. Fire resistant hydraulic fluids containing polyol esters are categorized as Type HFDU, and generally have an operating range of −20° C. to 150° C.

Various biodegradable hydraulic fluids have been synthesized to address this concern. TMP oleate (trimethylolpropane trioleate) is considered an industry standard in formulating biodegradable hydraulic fluids. It has the appropriate viscosity (approximately 46 cSt at 40° C.) and biodegradability. However, polyunsaturated fatty acid components in natural oil-derived TMP oleate are readily susceptible to oxidative and thermal degradation which may impact service life and additive formulation requirements. Thus, there is interest in natural oil-based unsaturated polyol esters that lack polyunsaturated impurities, which may serve as effective, biodegradable alternatives to TMP oleate for fire-resistant hydraulic fluids.

DETAILED DESCRIPTION OF THE INVENTION

The present application relates to the compositions and methods for synthesizing natural oil based unsaturated polyol esters that can be used in hydraulic fluid applications, including, without limitation, fire-resistant hydraulic fluid applications, marine hydraulic fluid applications, metalworking fluid applications, and transformer fluid applications. Such unsaturated polyol esters can be used as solely as base oil stocks, or blended with other synthetic fluids or additives. The base oil provides the primary lubricant functionality and performance. The additives enhance the performance of the base oil and also provide additional advantages and/or remove the shortcomings of the base oil. Suitable non-limiting examples of additives may include detergents, antiwear agents, antioxidants, metal deactivators, extreme pressure (EP) additives, dispersants, viscosity index improvers, pour point depressants, corrosion protectors, friction coefficient modifiers, colorants, antifoam agents, demulsifiers and the like.

In one aspect, the unsaturated polyol esters were prepared via the transesterification of unsaturated alkyl esters with a suitable polyhydric alcohol. Transesterification is well known to those skilled in the art and can be depicted by the following equation: $RCOOR^1 + R^2OH \rightarrow RCOOR^2 + R^1OH$. The reactant esters are commonly unsaturated fatty acid alkyl esters, including $C_5$-$C_{35}$ unsaturated fatty acid alkyl esters derived from a natural oil. In certain embodiments, the $C_5$-$C_{35}$ unsaturated fatty acid alkyl esters may be unsaturated fatty acid methyl esters. In further embodiments, such esters may include 9-DAME (9-decenoic acid methyl esters), 9-UDAME (9-undecenoic acid methyl esters), and/or 9-DDAME (9-dodecenoic acid methyl esters). The transesterification reaction is conducted at approximately 60-80° C. and approximately 1 atm.

Such unsaturated fatty acid alkyl esters are conveniently generated by self-metathesis and/or cross metathesis of a natural oil. Metathesis is a catalytic reaction that involves the interchange of alkylidene units among compounds containing one or more double bonds (i.e., olefinic compounds) via the formation and cleavage of the carbon-carbon double bonds. Generally, cross metathesis may be represented schematically as shown in Equation I:

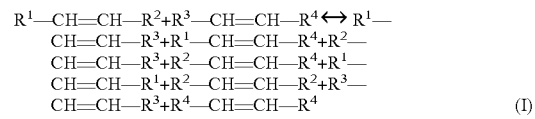

$$R^1-CH=CH-R^2 + R^3-CH=CH-R^4 \leftrightarrow R^1-CH=CH-R^3 + R^1-CH=CH-R^4 + R^2-CH=CH-R^3 + R^2-CH=CH-R^4 + R^1-CH=CH-R^1 + R^2-CH=CH-R^2 + R^3-CH=CH-R^3 + R^4-CH=CH-R^4 \quad (I)$$

wherein $R^1$, $R^2$, $R^3$, and $R^4$ are organic groups.

Generally, self-metathesis may be represented schematically as shown in Equation II below.

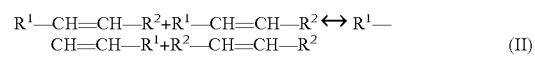

$$R^1-CH=CH-R^2 + R^1-CH=CH-R^2 \leftrightarrow R^1-CH=CH-R^1 + R^2-CH=CH-R^2 \quad (II)$$

wherein $R^1$ and $R^2$ are organic groups.

In particular, self-metathesis of natural oils or cross-metathesis of natural oils with olefins. Suitable olefins are internal or α-olefins having one or more carbon-carbon double bonds, and having between about 2 to about 30 carbon atoms. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof, and preferably α-olefins, and particularly ethylene, propylene, 1-butene, 1-hexene, 1-octene, and the like. Non-limiting examples of procedures for making unsaturated fatty acid alkyl esters by metathesis are disclosed in WO 2008/048522, the contents of which are incorporated herein by reference. In particular, Examples 8 and 9 of WO 2008/048522 may be employed to produce methyl 9-decenoate and methyl 9-dodecenoate. Suitable procedures also appear in U.S. Pat. Appl. Publ. No. 2011/0113679, the teachings of which are incorporated herein by reference.

The metathesis catalyst in this reaction may include any catalyst or catalyst system that catalyzes a metathesis reaction. Any known metathesis catalyst may be used, alone or in combination with one or more additional catalysts. Some metathesis catalysts may be heterogeneous or homogenous catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

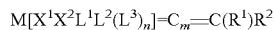

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

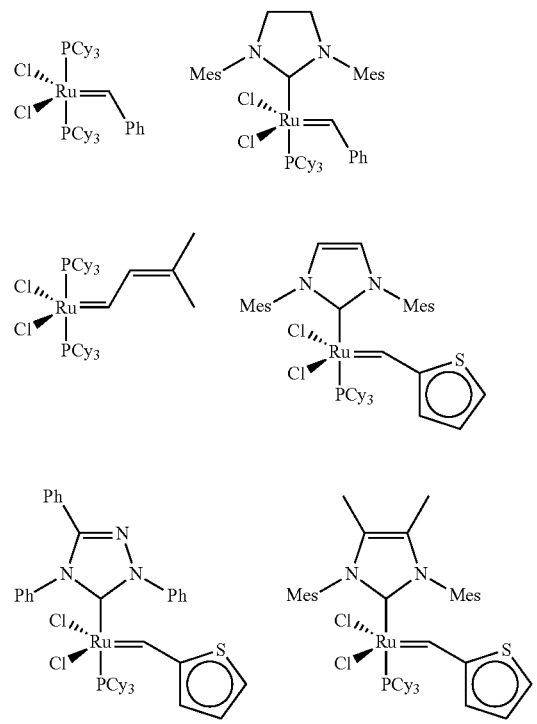

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/

0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

Natural oils suitable for use as a feedstock to generate the unsaturated fatty acid alkyl esters from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, linseed oil, tung oil, jatropha oil, mustard oil, pennycress oil, camellina oil, coriander oil, almond oil, wheat germ oil, bone oil, tallow, lard, poultry fat, fish oil, and the like. Soybean oil, palm oil, rapeseed oil, and mixtures thereof are preferred natural oils.

The unsaturated fatty acid alkyl esters were reacted with a suitable polyhydric alcohol. Such polyhydric alcohols include ethylene glycols, including di-, tri- and tetraethylene glycols; propylene glycols, including di-, tri-, and tetrapropylene glycols; glycerol; trimethylol propane; neopentyl glycol, ditrimethylolpropane, dipentaerythritol, bisphenol A, bisphenol F, bisphenol B, bisphenol S, 2,2-bis(4-hydroxycyclohexyl)propane, 1,1-, 1,2-, 1,3- and 1,4-cyclohexanedimethanol, 1,2-, 1,3- or 1,4-cyclohexanediol, butanediol, sorbitol, arabitol, mannitol, sucrose, fructose, glucose, erythritol, and pentaerythritols, including di- and tripentaerythritol. Preferably, the polyhydric alcohol is pentaerythritol (also referred to herein as "PE"), or trimethylol propane (also referred to herein as "TMP"). As understood by a person skilled in the art, various purity levels of the aforementioned polyhydric alcohols may be used to tailor a product with distinct physical properties. As a non-limiting example, an 88% purity pentaerythritol material may be used, and in other embodiments, a 98% purity pentaerythritol material may be used.

Suitable catalysts for the transesterification reaction include any acidic, non-volatile esterification catalysts, Lewis acids, Bronsted acids, organic acids, substantially non-volatile inorganic acids and their partial esters and heteropolyacids. Particularly suitable esterification catalysts include alkyl, aryl or alkaryl sulfonic acids, such as for example methane sulfonic acid, naphthalene sulfonic acid, p-toluene sulfonic acid, and dodecyl benzene sulfonic acid. Suitable acids may also include aluminum chloride, boron trifluoride, dichloroacetic acid, hydrochloric acid, iodic acid, phosphoric acid, nitric acid, acetic acid, stannic chloride, titanium tetraisopropoxide, dibutyltin oxide, and trichloroacetic acid. Other suitable catalysts for the transesterification reaction include any basic, non-volatile esterification catalysts. Suitable basic transesterification catalysts include metal or alkaline metal alkoxides and hydroxides, and sodium and potassium carbonates. These catalysts generally are used in quantities of from about 0.1 to 5 percent by weight of the natural oil starting material.

Examples

Synthesis of TMP Esters of 9-DAME and 9-DDAME

A 2 L 4-neck round-bottom flask equipped with a thermocouple and short-path vacuum distillation apparatus was charged with 9-DAME or 9-DDAME and sparged with nitrogen while stirring for 30 min. Next, TMP (0.256 equiv) and dibutyltin oxide (0.02 equiv) were added as solids, respectively. The resultant mixture was heated to 150° C. under mild vacuum (500 torr). The reaction was kept at 150° C. and the pressure was reduced to 100 torr until the desired conversion was observed by GC-FID. Excess 9-DAME or 9-DDAME was removed via distillation (200° C., 0.1 torr). The product was cooled to room temperature under vacuum and filtered over a plug of alumina oxide and diatomaceous earth to remove catalyst. Physical properties of 9-DAME (see 1 in Scheme 1) and 9-DDAME (see 2 in Scheme 1) compared with commercial TMP oleate 3 (Synative® ES TMP 05A, available from Cognis GmbH) are shown in Table 1. In Table 1 below, TAN is the total acid number, KV is the kinematic viscosity at 40° C. and 100° C. in cSt, VI is the viscosity index, PP is the pour point, the TGA is the thermogravimetric analysis, the IV is the iodine value, and the AP is the aniline point. As used herein in these Examples, TAN was measured by ASTM D664, KV was measured by ASTM D455, VI was measured by ASTM D2270, PP was measured by ASTM D97, TGA was measured by ASTM 6375-09, IV was measured by AOCS Cd 1d-92, and AP was measured by ASTM D611.

TABLE 1

Physical Properties of TMP Esters from 9-DAME and 9-DDAME

| TMP Ester | TAN | Kv 100° C. | Kv 40° C. | VI | PP | TGA | IV | Hydroxy Value | AP |
|---|---|---|---|---|---|---|---|---|---|
| 1 (9-DAME) | <1 | 4.67 | 20.36 | 154.26 | <−60 | 2.46 | 127.67 | 12.1 | <20 |
| 2 (9-DDAME) | <1 | 6.12 | 28.23 | 173.64 | −42 | 2.69 | 109.84 | 14.73 | <20 |
| 3 (Oleate) | 0.94 | 9.5 | 46.79 | 192.68 | −45 | 2.57 | 86.6 | 13 | — |

A synthesis scheme for making TMP esters of 9-DAME (1) and 9-DDAME (2) is shown below. These esters were synthesized via transesterification using a tin Lewis acid catalyst as shown in Scheme 1.

Scheme 1. Transesterification of 9-DAME and 9-DDAME with TMP.

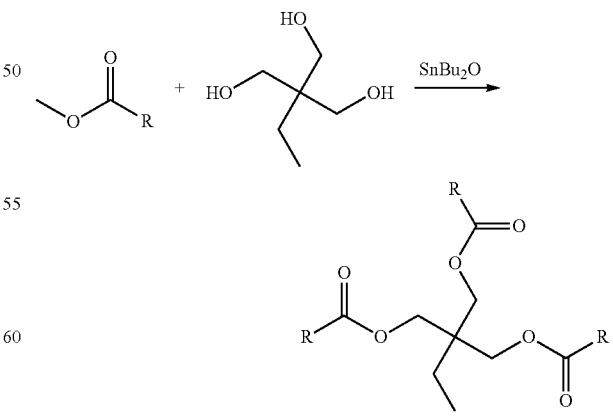

(1) R = $(CH_2)_7CH=CH_2$ (2) R = $(CH_2)_7CH=CHCH_2CH_3$

Testing of TMP Esters of 9-DAME and 9-DDAME

The starting efficiency of hydraulic motors is a critical and limiting criterion in hydraulic system design. Optimization of lubricant chemistry is one approach to improving starting efficiency. Improved performance was correlated with a lower pressure-viscosity coefficient and static and boundary friction coefficients. Additionally, oxidation is a critical mode of lubricant degradation. As a hydraulic fluid oxidizes, it forms acids and insoluble oxidation products, which can lead to formation of sludge or varnish. These degradation products can coat bearing and oil cooler surfaces, preventing adequate cooling of the bearings. Areas with tight tolerances such as hydraulic control valves can also become coated causing operational issues.

TMP esters derived from 9-DAME (see 1 in Scheme 1) and 9-DDAME (see 2 in Scheme 1) may show improved response to antioxidant over TMP oleate (due to the lack of polyunsaturated impurities common in oleate feedstocks) with similar or potentially improved lubricity under boundary lubrication conditions due to increased polarity. To test these assumptions, rotary pressure vessel oxidation tests (RPVOT), as measured by ASTM D2272, and ball-on-disc MTM friction tests were performed.

RPVOT is a rigorous oxidation test routinely employed on industrial oils. The oil sample, water, and copper catalyst coil are charged into a heated vessel and pressurized with oxygen. The vessel is rotated and lubricant oxidation onset is characterized in minutes by a drop in pressure. RPVOT oxidation test data for unsaturated polyol esters with 9-DAME, 9-DDAME, and methyl oleate dosed with varying amounts of antioxidant (AO) are shown in Table 2. In the absence of antioxidant (AO), each oil experienced an oxidation onset time ~15 min. Interestingly at 0.5% w/w AO, the TMP ester of 9-DAME (1) showed >8-fold increase in oxidative stability over commercial TMP ester of methyl oleate (3), while TMP ester of 9-DDAME (2) showed a similar response despite both 1 and 2 having higher IV values than 3. Increasing the AO loading to 1.5% w/w shows a similar trend between 1 and 3 but a roughly 2-fold improvement in 2 over 3. Digestion of 3 into fatty acid methyl ester constituents with sodium methoxide revealed 13% of the diene linoleate impurity. Notably, double bond position in the fatty acid chain has an influence beyond the lack of polyunsaturated diene impurities from TMP esters of 9-DAME as the terminal olefins in 1 enable some synergistic response to diphenylamine AO Irganox® L57 (from BASF) compared to 2 with an internal olefin. It is possible that the reduced number of allylic hydrogen oxidation sites in 1 are responsible.

TABLE 2

Oxidative Stability by RPVOT (ASTM D2272)

| | Time (min) | | |
|---|---|---|---|
| TMP Ester | 0% AO* | 0.5% AO* | 1.5% AO* |
| 1 (9-DAME) | 18 | 161 | 174 |
| 2 (9-DDAME) | 15 | 24 | 43 |
| 3 (Oleate) | 15 | 19 | 23 |

*Antioxidant (AO) L57 added in % w/w.

A friction bench testing protocol was designed to evaluate 1-3 using a PCS mini-traction machine (MTM). The test aimed to simulate low speed conditions experienced by hydraulic fluids which have been shown to correlate with hydraulic motor starting efficiency. Each TMP ester was blended with PAO (1:1 v/v) to a final KV 100° C.=6.7 cSt. The friction test consists of three steps and was run at three temperatures respectively, 50° C., 75° C., and 100° C. At each temperature, a load of 30N was applied between an AISI E52100 steel ball and a disc immersed in sample oil. Then, the ball was slid against the disc at 300 mm/s for 30 min to condition the contact surface. Subsequently, sliding was continued at 40 mm/s for 10 min to measure the low speed friction. The coefficient of friction was then averaged for each temperature and used as a measure of low speed friction for each oil sample.

The results of the friction tests are shown in Table 3 below, which shows a comparison of the low speed frictional properties of unsaturated polyol esters and commercial TMP oleate. Significantly, 9-DAME based 1 displays a pronounced lower coefficient of friction than both 2 and the commercial reference 3 at lower temperatures suggesting 1 may possess better starting efficiency in hydraulic fluid applications.

TABLE 3

| | Avg COF | | |
|---|---|---|---|
| 40 mm/s | 50° C. | 75° C. | 100° C. |
| 1 TMP 9-DAME | 0.061 | 0.062 | 0.071 |
| 2 TMP 9-DDAME | 0.084 | 0.097 | 0.092 |
| 3 TMP Oleate | 0.083 | 0.078 | 0.073 |

Synthesis of PE Esters of 9-DAME and 9-DDAME

A 500 mL 4-neck round-bottom flask equipped with a thermocouple, heating mantle, overhead stirrer, heated column, nitrogen inlet, and short-path vacuum distillation apparatus was charged with 9-DAME or 9-DDAME (4 equiv) and sparged with nitrogen while stirring for 15 min. Next, pentaerythritol (PE; 98% pure) (1 equiv) and dibutyltin oxide (0.1 wt. %) were added as solids, respectively. The resultant mixture was heated to 180° C. while maintaining a flow of nitrogen over the reaction surface (flow rate of ~1-1.5 lpm). The reaction was stirred (~500 rpm) at 180° C. for 8 hours and conversion was monitored through GC analysis hourly. An optional modification to the synthesis is during the final two hours of the reaction, the pressure is reduced to 200 torr. Upon cooling, the material was filtered through a fritted glass funnel over a plug of diatomaceous earth (bottom) and alumina oxide (top). If necessary, excess FAME was removed via distillation (250° C., 20 torr, 4 h). Physical properties of PE esters of 9-DAME 4 and 9-DAME 5 compared with commercial TMP oleate 3 (Synative® ES TMP 05A, Cognis) are shown in Table 4. In Table 4 below, TAN is the total acid number, KV is the kinematic viscosity at 40° C. and 100° C. in cSt, VI is the viscosity index, P.P. is the pour point, the TGA is the thermogravimetric analysis, the IV is the iodine value, and the AP is the aniline point. As used herein in these Examples, TAN was measured by ASTM D664, KV was measured by ASTM D455, VI was measured by ASTM D2270, PP was measured by ASTM D97, TGA was measured by ASTM 6375-09, IV was measured by AOCS Cd 1d-92, and AP was measured by ASTM D611.

TABLE 4

Physical Properties of PE Esters from 9-DAME and 9-DDAME

| PE Ester | TAN | Kv 100° C. | Kv 40° C. | VI | P.P. | TGA | IV | Hydroxy Value | Flash Point COC (° C.) |
|---|---|---|---|---|---|---|---|---|---|
| 4 (9-DAME) | <1 | 6.96 | 33.48 | 175.41 | −18 | 0.66 | — | 5.86 | |
| 5 (9-DDAME) | <1 | 8.87 | 46.65 | 173.42 | −9 | 0.49 | 100-120 | (7-11) | 313 |
| 3 (IMP-Oleate) | 0.94 | 9.5 | 46.79 | 192.68 | −45 | 2.57 | 86.6 | 13 | ≥300 |

A synthesis scheme for making PE esters of 9-DAME (4) and 9-DDAME (5) are shown below. These esters were synthesized via transesterification using a tin Lewis acid catalyst as shown in Scheme 2.

Scheme 2. Transesterification of 9-DAME and 9-DDAME with PE.

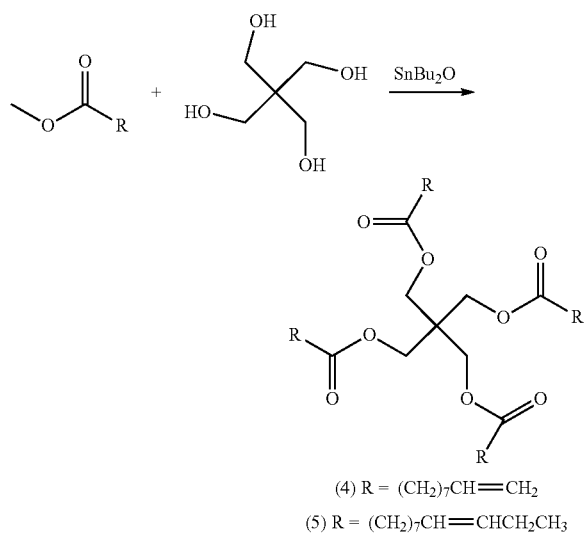

(4) R = (CH$_2$)$_7$CH═CH$_2$
(5) R = (CH$_2$)$_7$CH═CHCH$_2$CH$_3$

Product ester 5 meets ISO 46 viscosity grade similar to TMP-oleate

Testing of PE Esters of 9-DAME and 9-DDAME

Commercial requirements for fire resistant hydraulic fluids demand a viscosity in the ISO 46 range (KV at 40° C. of between 41.4 and 50.6) and a flash point above 300° C. As shown in Table 4, the PE 9-DDAME 5 material was the most suitable for such a purpose. Additionally, as demonstrated with the TMP esters derived from 9-DAME (see 1 in Scheme 1) and 9-DDAME (see 2 in Scheme 1), we believe that PE esters derived from 9-DAME (see 4 in Scheme 2) and 9-DDAME (see 5 in Scheme 2) may show improved antioxidant response over TMP oleate (due to the lack of polyunsaturated impurities common in oleate feedstocks). Therefore, rotary pressure vessel oxidation tests (RPVOT), as measured by ASTM D2272, were performed.

RPVOT oxidation test data for unsaturated polyol esters with 9-DAME, 9-DDAME, and methyl oleate dosed with varying amounts of antioxidant (AO) are shown in Table 5. In the absence of antioxidant (AO), each oil experienced an oxidation onset time ~30 min. The addition of 0.5% w/w AO Irganox® L57 did not improve overall oxidation resistance. However, at an AO loading of 0.5% w/w L57 and 0.5% w/w AO Irganox® L135, The PE ester of 9-DDAME (5) showed ~3-fold increase in oxidative stability over TMP oleate (3).

Lack of polyunsaturated diene impurities in the PE 9-DDA ester and a synergistic response to a mixture of diphenylamine AO Irganox® L57 and phenolic AO Irganox® L135 (both from BASF) have resulted in the increased oxidative stability.

TABLE 5

Oxidative Stability by RPVOT (ASTM D2272)

| | Time (min) | | |
|---|---|---|---|
| PE Ester | 0% AO* | 0.5% AO* | 0.5% AO* + 0.5% AO' |
| 5 (9-DDAME) | 31 | 39 | 101 |
| 3 (Oleate) | 30 | 33 | 36 |

*Antioxidant (AO*) 157 and Antioxidant (AO') L135 added in % w/w.

A key physical property of fire resistant hydraulic fluids is the possession of a high flash point (>300° C.). To determine if the PE 9-DDAME ester 5 met the flash point specifications, flash and fire point analysis, as measured by ASTM D92, was performed.

Flash and fire point analysis is commonly utilized for hydraulic fluid analysis. Flash point is the measure of the susceptibility of a sample to ignite in air under high heat and can indicate the possible presence of exceedingly volatile and flammable materials. The oil sample was charged into an open cup and heated at a controlled rate. At pre-determined intervals, a flame was passed over the cup. The flash point was determined as the lowest temperature at which the vapors of the oil ignite. Fire point was determined by continuing the heating of the sample until a temperature was reached at which the flame ignites the sample and burns for 5 seconds. PE 9-DDAME (5) has demonstrated a flash point >300° C., and in some embodiments, from 300° C. to 340° C.

The hydrolytic stability of a hydraulic fluid is of significant importance. Fluids that are unstable will form particles and acidic impurities which can have a detrimental effect on hydraulic systems, resulting in a malfunctioning system due to corrosion, changes in viscosity, or valve sticking. Therefore, the hydrolytic stability of PE 9-DDAME (5) was measured by ASTM D2619. The analysis was conducted by sealing the neat sample, water, and a copper test specimen in a pressure-type glass beverage bottle. The bottle is heated to 93° C. in an oven while rotating end over end for 48 hrs. The organic and aqueous layers are then separated and any particles are weighed. The acidity of the water and organic layers are analyzed, as well as the viscosity of the oil and the weight of the copper. Change in any of these analyses determine the hydrolytic stability of the sample. The greater the change, the less stable the material was.

The results of the hydrolytic stability test are shown in Table 6. The results concluded there was not sufficient hydrolysis of the either material to cause corrosion.

TABLE 6

Hydrolytic Stability (ASTM D-2619)

| Sample ID | Weight change of copper panel (mg/cm²) | Appearance of copper panel | % Change in viscosity (@ 40° C. cSt) | Change in acid number (mg KOH/gram) | Total acidity of water layer (mg KOH/gram) | % insoluble |
|---|---|---|---|---|---|---|
| Pentaerythritol (PE)-9DDAME (ID 1176-118) | −0.142 | Shiny 1B | −0.49 | 4.41 | 0.84 | 0.005 |
| Commercial TMP ester Synative ® ES 2964 | −0.242 | Shiny 1B | 0.49 | 0.40 | 3.65 | 0.003 |

Additional predictive testing, through Estimation Program Interface (EPI) Suite from the U.S. Environmental Protection Agency, has shown that the PE-9DDAME material has a ready biodegradability prediction of yes, and a total removal in wastewater treatment of 94.04%.

Synthesis of PE Esters of 9-DDAME with Saturated Linear and/or Branched Acids or their Corresponding Alkyl Ester Substituents.

In some aspects, the synthesis of PE esters of 9-DDAME may occur with various saturated fatty acids. The saturated fatty acid may be a C3 to C35 linear chain or branched saturated fatty acid. Some non-limiting examples of straight chain saturated fatty acids include propionic, butyric, valeric, caproic, enanthic, caprylic, pelargonic, capric, undecylic, lauric, tridecylic, myristic, pentadecanoic, palmitic, margaric, stearic, nonadecyclic, arachidic, heneicosylic, behenic, tricosylic, lignoceric, pentacoyslic, cerotic, heptacosylic, carboceric, montanic, nonacosylic, melissic, lacceroic, psyllic, geddic, ceroplastic acids. Some non-limiting examples of branched saturated fatty acids include isononanoic acid (a mixture of isomers with a 3,5,5-trimethylhexanoic acid content of about 90%), isodecanoic acid, isotridecanoic acid, 2-ethyl hexanoic acid, isostearic acid, neodecanoic acid, neononanoic acid, neoundecanoic acid, isovaleric acid, pivalic acid, isomer variants of the preceding, and the like. In some aspects, the corresponding alkyl esters of such saturated fatty acids, including methyl esters, may be utilized.

Scheme 3 shows a general synthesis to prepare unsaturated polyol esters with saturated linear and/or branched acids or their corresponding alkyl ester substituents.

Scheme 3.
Synthesis of polyol ester saturated acid or alkyl ester substituents.

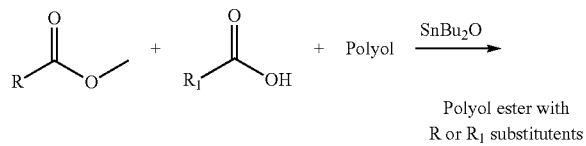

Polyol ester with R or R₁ substitutents

In Scheme 3 above, R above is a C5 to C35 unsaturated alkyl group to provide a C5 to C35 unsaturated fatty acid alkyl ester. R₁ above is a C5 to C35 linear or branched alkyl group to provide a C5 to C35 linear or branched saturated fatty acid, or alternatively the corresponding alkyl esters of the saturated linear or branched acids.

The following general procedure was typically employed for the synthesis of PE esters of 9-DDAME with saturated linear and/or branched acids. A 1 L 3-neck round-bottom flask equipped with a thermocouple, heating mantle, overhead stirrer or stir bar, nitrogen inlet, and short-path vacuum distillation apparatus was charged with 9-DDAME (3.84-4.56 equiv) and PE (1 equiv) respectively, and sparged with nitrogen while stirring for 30 min at 60° C. Next, dibutyltin oxide (0.1 wt %) was added as a solid. The resultant mixture was heated to 210° C. (takes ~1 hr to reach temperature) with a slight nitrogen head flow. Once an hour into heating above 60° C. has lapsed, the desired acid (or its corresponding alkyl ester) (0.96-0.24 equiv) was carefully added to the reaction via syringe. The total equivalents of reagent (ester and acid) to PE should be 4.8:1 (or 1.2 equivalents reagent per hydroxyl on PE). The reaction was stirred (~500 rpm) at 210° C. for 8-10 hours and conversion was monitored through GC analysis hourly. An optional modification to the synthesis was during the final two hours of the reaction, the pressure was reduced to 200 torr. If necessary, excess FAME and acid was removed via distillation (230° C., 20 torr, 3 h). The reaction was then cooled to 100° C. and the vacuum was broken with nitrogen to allow for the addition of oxalic acid dehydrate (0.3 wt %). Vacuum was re-initiated and the material was allowed to heat and stir for 1 hour. Upon cooling, the material was filtered through a fritted glass funnel over a plug of diatomaceous earth (bottom) and basic aluminum (top). Physical properties of various polyol esters derived from PE compared with commercial TMP oleate (Synative® ES TMP 05A, Cognis) are shown in Table 8 below.

Another commercial requirement for many industrial applications was a product which possessed a pour point <−20° C. PE 9-DDAME (5) has a pour point of −9° C. (see 5 in table 4). Following the previous process, various linear and branched saturated esters were utilized in an attempt to lower the pour point properties of the final PE ester. Four various linear and/or branched acids were attempted and isononanoic acid was successful in lowering the pour point <−20° C. (See Table 7). Product esters 5 and 6 meet ISO 46 viscosity grade similar to TMP-oleate, but ester 6 possesses a more desirable pour point over ester 5 in comparison to TMP-oleate. Therefore, characterization and further experimentation was conducted only on PE ester 6 as shown in Table 8. As used herein in these Examples, TAN is measured by ASTM D664, KV is measured by ASTM D455, VI is measured by ASTM D2270, PP is measured by ASTM D97, TGA is measured by ASTM 6375-09, IV is measured by AOCS Cd 1d-92, and AP is measured by ASTM D611.

TABLE 7

Pour Point of PE Esters

| PE9-DDAME with Acid | P.P. (° C.) |
|---|---|
| Isononanoic acid | −21 |
| Neodecanoic acid | −9 |
| 2-ethyl hexanoic acid | −9 |
| C-670 | −9 |

C-670 is a mix of caproic and caprylic acids available from P & G Chemicals.

TABLE 8

Physical Properties of PE esters with saturated and unsaturated linear and branched constituents

| PE Ester | TAN | KV 100° C. | KV 40° C. | VI | P.P. (° C.) | TGA | IV | Hydroxy Value | Flash Pt. COC (° C.) |
|---|---|---|---|---|---|---|---|---|---|
| 6 9-DDAME/ Isononandic acid | 0.5 | 8.32 | 45.61 | 159.71 | −21 | 1.33 | — | — | |
| 5 9-DDAME | 0.11 | 8.87 | 46.65 | 173.42 | −9 | 0.49 | — | (7-11) | 313 |
| 3 TMP-Oleate | 0.94 | 9.5 | 46.79 | 192.68 | −45 | 2.57 | 86.6 | 13 | ≥300 |

Scheme 4 shows the one-pot esterification and transesterification method employed to prepare PE esters from blends of 9-DDAME with saturated linear and/or branched acids or their corresponding alkyl esters.

Scheme 4. Synthesis of PE polyol esters from blends of 9-DDAME and saturated linear or branched fatty acids.

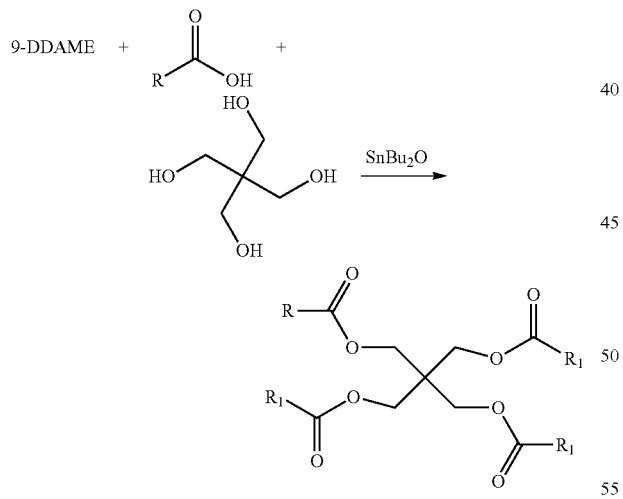

In Scheme 4 above, R is a C5 to C35 linear or branched alkyl group to provide C3 to C35 linear or branched saturated fatty acid, or alternatively the corresponding alkyl esters of the saturated linear or branched acids. $R_1$ above may be a C11 unsaturated linear alkyl chain, to provide a 9-DDAME substituent group. In the alternative, a C9 unsaturated linear alkyl chain may also be used to provide a 9-DAME substituent group, and a C10 unsaturated linear alkyl chain may also be used to provide a 9-UDAME substituent group.

Additional Experimentation and Testing

Certain unsaturated polyol esters were analyzed under: (i) Twist Compression Tests, (ii) Microtap Analysis, (iii) Pin and Vee Block Tests, and (iv) Four Ball Wear Tests.

The Twist Compression Test is a boundary lubrication test designed to measure friction and evaluate adhesion in metalforming. In this test, an annular specimen contacts a flat specimen retained in a horizontal position. The lower, flat specimen is raised under a preset hydraulic pressure while the annular specimen is rotated. Friction is calculated from a measured torque and a known normal load. Both specimens can be inspected for metal transfer and surface damage.

The Microtap Analysis measures spindle torque when tapping various metals to determine lubricant effectiveness.

The Pin and Vee Block Test is a machine which measures wear, friction and extreme pressure properties of materials and lubricants. The machine rotates a ¼ inch diameter test pin (journal) against two ½ inch diameter vee blocks. A four line contact region is established as load is applied through a mechanical gage by a ratchet wheel and an eccentric arm.

The Four Ball Wear Test is a method which is used to determine the relative wear-preventing properties of lubricating fluids in sliding and rolling applications. Three ½ inch diameter steel balls are clamped together and covered with the test lubricant. A fourth ½ inch diameter steel ball is pressed into the cavity formed by the three clamped balls for three point contact, and rotated for a set duration. Lubricants are compared using the average size of the scar diameters worn on the three lower clamped balls.

Twist Compression Tests on Cold Rolled Steel

| Lubricant Additive at 18.5% treat in formulated concentrate | Sample ID | Friction Avg | Friction Std Dev | Time to Breakdown (seconds) Avg | Time to Breakdown (seconds) Std. Dev | Friction Factor |
|---|---|---|---|---|---|---|
| 5 PE-9DDAME | 1206-50-1 | 0.149 | 0.005 | 12.38 | 0.762 | 84 |
| High oleic canola oil (Agri Pure 85) | 1206-50-2 | 0.139 | 0.007 | 13.8 | 2.292 | 100 |
| Commercial TMP oleate Synative ® ES 2964 | 1206-50-3 | 0.146 | 0.002 | 11.09 | 1.214 | 77 |
| Afton Actralube 8330 | 1206-50-4 | 0.174 | 0.003 | 2.35 | 0.193 | 14 |

Twist Compression Tests on Aluminum 6061

| Lubricant Additive at 18.5% treat in formulated concentrate | Sample ID | Friction Avg | Std Dev | Time to Breakdown (seconds) Avg | Std. Dev | Friction Factor |
|---|---|---|---|---|---|---|
| 5 PE-9DDAME | 1206-50-1 | 0.156 | 0.007 | 3.540 | 0.918 | 23 |
| High oleic canola oil (Agri Pure 85) | 1206-50-2 | 0.161 | 0.01 | 76.720 | 34.920 | 482 |
| Commercial TMP oleate Synative ® ES 2964 | 1206-50-3 | 0.149 | 0.006 | 45.370 | 14.154 | 302 |
| Afton Actralube 8330 | 1206-50-4 | 0.155 | 0.003 | 0.250 | 0.062 | 2 |

Microtap Analysis (ASTM D5619)

High Oil Semisynthetic. 10% Lubricant in Concentrate, diluted to 10% in DI Water. Tests were run at 300 RPM.

| Lubricant Additive at 10% treat in formulated concentrate | Sample ID | 6061 Aluminum M6 Forming Tap Avg Torque Ncm | Std Dev | 1018 Cold Rolled Steel M6 Forming Tap Avg Torque Ncm | Std. Dev |
|---|---|---|---|---|---|
| 5 PE-9DDAME | 1206-50-1 | 164.1 | 82.3 | 199.6 | 74.9 |
| High oleic canola oil (Agri Pure 85) | 1206-50-2 | 162.3 | 81.6 | 193.3 | 70.7 |
| Commercial TMP oleate Synative ® ES 2964 | 1206-50-3 | 157.8 | 79.9 | 200.8 | 73.6 |
| Afton Actralube 8330 | 1206-50-4 | 157.9 | 79.4 | 197.1 | 71.5 |

Comparison to Commercial Esters—Pin and Vee Block Test (ASTM D3233A) and Four Ball Wear Test (ASTM 04172)

In the chart below, EP refers to extreme pressure, and COF refers to coefficient of friction

| Lubricant Additive at 18.5% treat in formulated concentrate | Sample ID | EP Property (Pin and Vee Block test) Failure Load (lb) Run 1 | Run 2 | Avg | Std Dev | Four-Ball Results Avg. Wear scar diameter (mm) | Wear scar range | COF | COF range |
|---|---|---|---|---|---|---|---|---|---|
| 5 PE-9DDAME | 1206-50-1 | 3684 | 3553 | 3619 | 92.6 | 0.744 | 0.719-0.773 | 0.080 | 0.070-0.084 |
| High oleic canola oil (Agri Pure 85) | 1206-50-2 | 3803 | 3727 | 3765 | 53.7 | 0.551 | 0.509-0.596 | 0.081 | 0.072-0.085 |
| Commercial TMP oleate Synative ® ES 2964 | 1206-50-3 | 3788 | 3728 | 3758 | 42.4 | 0.674 | 0.633-0.726 | 0.081 | 0.068-0.085 |
| Afton Actralube 8330 | 1206-50-4 | 3986 | 3905 | 3946 | 57.3 | 0.541 | 0.506-0.583 | 0.078 | 0.071-0.082 |

The foregoing detailed description, examples, and accompanying figures have been provided by way of explanation and illustration, and are not intended to limit the scope of the invention. Many variations in the present embodiments illustrated herein will be apparent to one of ordinary skill in the art, and remain within the scope of the invention and their equivalents. The skilled person in the art will recognize many variations that are within the spirit of the invention and scope of any current or future claims.

The invention claimed is:

1. An unsaturated polyol ester composition comprising a compound of the following structure:

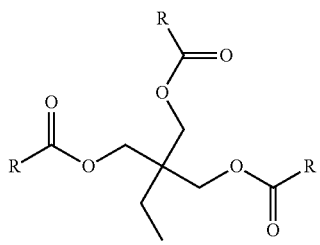

wherein R is $(CH_2)_7CH=CH_2$ or $(CH_2)_7CH=CHCH_3$.

2. The unsaturated polyol ester composition of claim 1, wherein the composition is a hydraulic fluid.

3. The unsaturated polyol ester composition of claim 1, wherein R is $(CH_2)_7CH=CH_2$.

4. The unsaturated polyol ester composition of claim 1, wherein R is $(CH_2)_7CH=CHCH_3$.

5. An unsaturated polyol ester composition comprising a compound of the following structure:

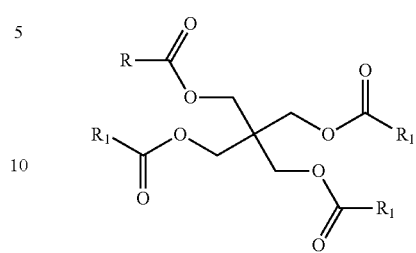

wherein R is an unsaturated C9 linear alkyl group, and each $R_1$ is independently the hydrocarbyl moiety of a C3 to C35 linear or branched saturated fatty acid selected from the group consisting of isononanoic acid, neodecanoic acid, 2-ethylhexanoic acid, caproic acid, and caprylic acid.

6. The unsaturated polyol ester composition of claim 5, wherein R is $(CH_2)_7-CH=CH_2$.

* * * * *